United States Patent [19]

Marchetti

[11] 4,112,733

[45] Sep. 12, 1978

[54] DEVICE FOR MONITORING ABSOLUTE VELOCITY OF POINTS OF DRIVEN PILES DURING IMPACT

[76] Inventor: Silvano Marchetti, Via Bracciano, 38, Rome, Italy

[21] Appl. No.: 785,292

[22] Filed: Apr. 6, 1977

[30] Foreign Application Priority Data

Apr. 6, 1976 [IT] Italy .............................. 48881 A/76

[51] Int. Cl.² .............................................. G01N 3/34
[52] U.S. Cl. ........................................ 73/12; 73/519; 324/160
[58] Field of Search ................... 73/519, 518, 71.2, 12, 73/84, 11, 520; 336/130; 324/160, 163, 176

[56] References Cited

U.S. PATENT DOCUMENTS

3,535,919  10/1970  Budlong et al. ........................ 73/84

FOREIGN PATENT DOCUMENTS

801,383  12/1968  Canada ..................................... 73/518

Primary Examiner—Jerry W. Myracle
Attorney, Agent, or Firm—Holman & Stern

[57] ABSTRACT

A magnetic core velocity transducer is attached to a metallic base plate by means of non-ferrous support elements. Relative movement of the coil over the core of the velocity transducer, during impact of a driven pile to which the base plate is rigidly attached, generates a voltage at the transducer terminals which is proportional to the relative velocity between the core and the coil.

3 Claims, 3 Drawing Figures

DEVICE FOR MONITORING ABSOLUTE VELOCITY OF POINTS OF DRIVEN PILES DURING IMPACT

BACKGROUND OF THE INVENTION

The present invention relates to a device which enables the direct monitoring of the absolute velocity of points of a driven pile during the impact between a hammer and the pile head.

The usefulness of knowing the velocity pulses during impact is well known to engineers, who use such pulses to obtain indications on pile load capacity, distribution of side friction along the pile, driving efficiency, etc.

At present, velocity pulses are determined indirectly, by using accelerometers rigidly attached to pile walls or to the pile tip. The accelerations are then integrated with respect to time to obtain velocities. The integration, simple in principle, creates in practice serious problems, so that very seldom are accurate velocity measurements obtainable, unless sophisticated and costly equipment, together with highly trained technicians, are employed.

On the other hand, the direct measurement of velocities of pile points, for instance with velocity transducers, would require that a fixed reference point be available, for measuring velocities with respect to it. Such a fixed reference point is normally unavailable, as the soil surface around the pile is kept on vibrating by the impacts, which occur about one per second. Moreover, even if the soil surface was vibration-free, a velocity measuring device should be reset very frequently, i.e. each time the increment of pile penetration equals the stroke of the impacting device.

Similar inconveniences, often more severe, are found when it is attempted to obtain velocity as a derivative of the displacement with respect to time.

In seismic and geophysical measurements, devices called geophones are used. The geophones are basically core and coil transducers where one of the two sliding elements is connected to a spring-supported mass, which is considered stationary as a first approximation. The geophones, however, are not suitable for measuring velocities of points of driven piles, where net displacements are much larger than seismic ones; moreover, in the case of driven piles, the spring supported mass would be vibrating without control.

SUMMARY OF THE INVENTION

The object of the present invention is to provide a device which overcomes the above mentioned drawbacks, allowing the direct measurement of the absolute velocities of points of driven piles to which the device is rigidly attached.

The concept on which the device is based is to measure the velocity of the pile point under observation relative to a freely falling object, the velocity of which is known: if $g$ is the gravity acceleration and $t$ is the time elapsed since the beginning of the free fall, the latter velocity is $g \times t$. The term $g \times t$ must be added to the measured relative velocity in order to obtain the required absolute velocity.

BRIEF DESCRIPTION OF THE DRAWINGS

The invention will be further described in regard to a non-limiting preferred embodiment with reference to the accompanying drawings in which.

DETAILED DESCRIPTION OF THE PREFERRED EMBODIMENT

Figure 1:
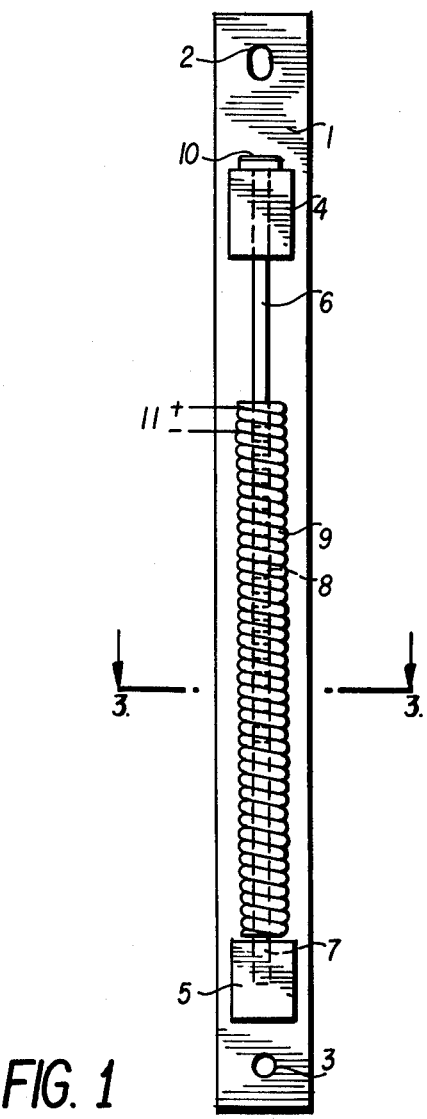
FIG. 1 is a frontal view of the device according to the invention.
Figure 2:
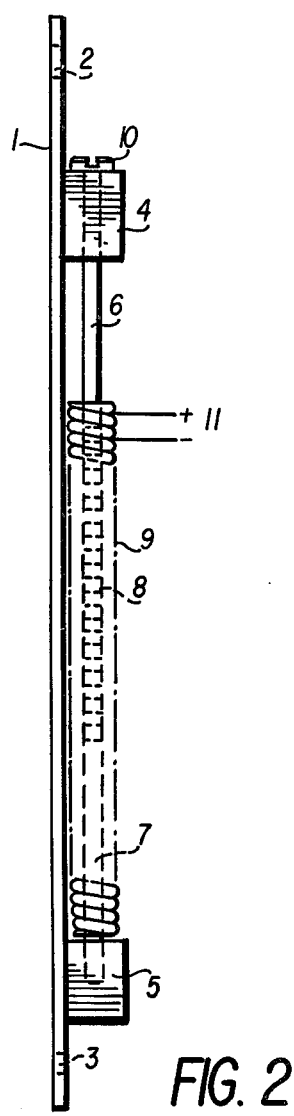
FIG. 2 is a side view of the device according to the invention.
Figure 3:
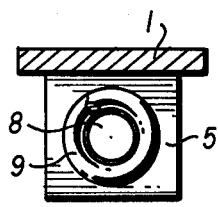
FIG. 3 is a plan view of the device according to the invention.

A rectangular metallic base plate 1, in vertical position, is rigidly attached to the pile surface, for instance by means of bolts inserted through holes 2 and 3. Two parallelepipedal blocks 4 and 5 are welded to the base plate and hold in position cylinders 6 and 7, which sustain a magnetic core 8 (or series of cores), having equal outside diameters. The blocks and cylinders 4-7 are made of a non-ferrous material, such as brass, in order to avoid demagnetization of the core. A hollow coil 9, cylinder in shape, is supported at rest by the block 5. The coil 9 and the core 8 are elements of a commercial velocity transducer; the voltage generated at transducer terminals 11 is proportional to the relative velocity between the core and the coil.

It is possible to withdraw or to insert the cylinders 6, 7 and the core 8, so that the coil 9 can be mounted by unscrewing a screw 10 at the top of the block 4. By tightening the screw 10, the cylinders 6, 7 and the core 8 become unitary with the plate 1: the only possible relative movement within the device is the sliding of the coil 9 longitudinally along the core 8, at a distance such as not to touch the vertical base plate 1.

When the point of the pile at which the base plate 1 is attached starts moving downwards, following hammer impact, the coil, no more sustained, drops with a velocity $g \times t$. Since the voltage generated at the coil terminals is proportional to the relative velocity between the core and the coil, to obtain the required absolute velocity the term $g \times t$ is added to the velocity pulse.

For instance, if the measured pulse is visualized using an oscilloscope, in order to obtain the absolute velocity, it must be added to the displayed diagram a line passing through the origin and having a slope equal to $g$.

The device also has the advantage that it does not need to be reset after each impact; nor does it need any excitation voltage.

I claim:

1. A device for the measurement of the absolute velocity of a driven pile during hammer impact comprising: a base plate adapted to be rigidly attached to a pile; a magnetic core velocity transducer comprising a magnetic core, a hollow coil surrounding the core and terminals, the axis of the velocity transducer being aligned in the direction of movement of the pile during impact; and support means rigidly attached to the base plate and rigidly supporting the core of the velocity transducer so that during impact of the pile only relative movement of the coil over the core occurs which generates a voltage at the transducer terminals proportional to the relative velocity of the transducer with respect to the pile.

2. The device as claimed in claim 1, wherein the support means are made of a non-ferrous material.

3. The device as claimed in claim 1, wherein the support means comprise two support blocks rigidly attached to the base plate; and two cylinders adapted to rigidly support the magnetic core therebetween, one of the cylinders being rigidly supported in each of the blocks and each of the cylinders having an outside diameter equal to the outside diameter of the magnetic core.

* * * * *